United States Patent [19]
Myers et al.

[11] Patent Number: 5,981,728
[45] Date of Patent: Nov. 9, 1999

[54] DULL1 CODING FOR A NOVEL STARCH SYNTHASE AND USES THEREOF

[75] Inventors: Alan M. Myers, Ames; Martha G. James, Des Moines, both of Iowa

[73] Assignee: Iowa State University Research Foundation, Ames, Iowa

[21] Appl. No.: 08/968,542

[22] Filed: Nov. 12, 1997

[51] Int. Cl.[6] .............................. C12N 15/29; C12N 5/04; C12N 15/82; A01H 5/00
[52] U.S. Cl. ...................... 536/23.6; 536/23.1; 435/69.1; 435/468; 435/469; 435/410; 435/419; 435/418; 435/412; 800/278; 800/284; 800/295; 800/320.1
[58] Field of Search .................................. 536/23.6, 23.1; 800/205, 278, 284, 295, 320.1; 435/69.1, 468, 469, 410, 419, 418, 412

[56] References Cited

PUBLICATIONS

Matzke et al. Plant Physiol. 1995. 107:679–685.
Napoli et al. The Plant Cell. 1989. vol. 2: 278–289.

*Primary Examiner*—Gary Benzion
*Assistant Examiner*—Ousama M-Faiz Zaghmout
*Attorney, Agent, or Firm*—Benjamin Aaron Adler

[57] ABSTRACT

The maize gene dull1 (du1) of the present invention is a determinant of the structure of endosperm starch. Mutations of du1 affect the activity of at least two enzymes involved in starch biosynthesis, namely the starch synthase, SSII, and the starch branching enzyme, SBEIIa. Du1 codes for a predicted 1674 residue protein, and is expressed with a unique temporal pattern in endosperm but is undetectable in leaf or root. The size of the Du1 product and its expression pattern match precisely the known characteristics of maize SSII. The Du1 product contains two different repeated regions in its unique amino terminus, one of which is identical to a conserved segment of the starch debranching enzymes. The cDNA provided for in the present invention encodes SSII, and mutations within this gene affect multiple aspects of starch biogenesis by disrupting an enzyme complex containing starch synthase(s), starch branching enzyme(s), and possibly starch debranching enzyme(s).

5 Claims, 13 Drawing Sheets

```
DU1                                    MEMVLRSQSPLCLRSGPVLIFRPTVAGGGG                                30

DU1     GTQSLLRTTRFARRRVIRCVVASPGCPNRKSRTASPNVKVAAYSNYAPRLLVESSSKKS                                  89

DU1     EHHDSSRHREETIDTYNGLSGSDAAELTSNRDVEIEVDLQHISEEELPGKVSINASLGE                                 148

DU1     METVDEAEVEEDKFEVDTSGIVLRNVAVREVDPKDEHNAKDVFVVDSSGTAPDNAAVEE                                 207

DU1     VVDEAEVEEDMVDVDILGLDLNNATIEEIDLMEEALLENFDVDSPGNASSGRTYGGVDE                                 266

DU1     LGELPSTSVDCIAINGKRRSLKPKPLPIVRFQEQEQIVLSIVDEEGLIASSCEEGQPVV                                 325

DU1     DYDKQEENSTAFDEQKQLTDDFPEEGISIVHFPEPNNDIVGSSKFLEQKQELDGSYKQD                                 384

DU1     RSTTGLHEQDQSVVSSHGQDKSIVGVPQQIQYNDQSIAGSHRQDQSIAGAPEQIQSVAG                                 443

DU1     YIKPNQSIVGSCKQHELIIPEPKKIES T ISYNEIDQSIVG S HKQDK S VVSVPEQIQSIV                           502
SS3            MDVPFPLHRSLSCTSVSNAITHLK I KPILGFVSHGTT S LSVQS S SWRKDGMVTGVS                        56

DU1     SHSKF N S TVDSYRQAESIIGVPEKVQSITSYDKLDQSIVSL K QDEPIISVPEKIQSI                              561
SS3     FSICA N FS GRRRRKVSTPRSQGSSPKGFVPRKPSGMSTQRKVQ K SNGDKESKSTSTKE                            115

DU1     VHYTKPNQSIVGLPKQQQSIVH T M EPKQSIDGFPKQDI S IVG I SNEFQTKQLAT V GTHD                        620
SS3     SEISNQKTVEARVETSDDDTKGV M RDHKFLEDEDEINQ STKS L S MSPVRVSSQF V ESEE                         174

DU1     GLLMKGVEA R ETSQKTEGDTLQATFN V DNLSQKQE G L T KEADEITTIEKINDEDLVMIE                         679
SS3     TGGDDKDAV K LNKSKRSEESGFIIDS V REQSGSQ GF I NASSKGSHAVGTKLYEILQVD                          233

FIGURE 6A-1
```

```
DU1  EQKSIAMNEEQTIVTEEDIPMAKVEIGIDKAKFLFLLSFEESSWDENEVGIIEADQYE   738
SS3  VEPQQLKENNAGNVEYKGPVASKLLEITKASDVEHTSNEIDDLDTNSFFKSDLIEEDE   292

DU1  VDETSMSTEQIQESPNDDLDPQALWSMLQELAEKNYSLGNKFTYPDVLKADSTIDLY    797
SS3  PLAAGTVETQSSLNLRLEMEANLRRQAIERLAEENLLQGIRLECFEEMVKPDEDVEIF   351

DU1  FNRDLSAVANEPDVLIKGAFNGWKRFFTEKHKSELAGDWWCCKLYIPKQAYRMDFVF    856
SS3  LNRGLSTLKNESDVLIMGAFNEMRYRSETTRLTETHLNGDWWSCKIHVPKEAYRADFVF  410

DU1  FNGHTVYIENNNNDFVIQIESTMDENLFEDFLAEEKQRELENLANEEAERRQTDEQRR   915
SS3  FNGQDVYDNDGNDFSITVKGGMQIIDEENELLEEKWREQEKLAKEQAEERLAEEQRR    469

DU1  MEEERAADKADRVQAKVEVETKKNKICNVLGIARAPVDNLWYIEPITTGQFATVRLYYN  974
SS3  IEAEKAEIEADRAQAKEEAAKKKKVLRELMVKATKTRDITWYIEPSEFKCEDKVRLYYN  528

DU1  INSRPIMSTEIMHGGYNNMIDGLSFAERLVHHHDKDCDWWFADVVPERTYVLDWVF    1033
SS3  KSSGPLSHAKDIMIHGGYNNWKDGLSIVKKLVKSERIDGDWWYTEVVIPDQALFLDWVF  587

DU1  ADGPPGSARNYDNNGGHDFHATLPNMTEFYWMEEEQRHYTRLQERRREEAIKRKA    1092
SS3  ADGPEKHAIAYDNNHRQDFHAIVPNHIPEELYWMEEEHQIFKTLQFERRLREAAMRAKV  646

DU1  ERNAKMKAEMKEKTMRMFLMSQKHIVYTEPLEIHAGTTIDVLYNPSNTVLIGKPEVWFR 1151
SS3  EKTALLIKNEIKERIMKSFLISQKHVVYTEPLIDIQAGSSVTVYYNPANTVLNGKPEIWFR 705

DU1  CSFNRMYPGVLPPQKMVQAENGSHLKATVYVPRDAYMMDFVFSESEEGGIYDNRNGL   1210
SS3  CSFNRMTHRLGPLPPQKMSPAENGIIHVRATVKVPLDAYMMDFVFSEREDGGIFDNKSGM 764

DU1  DYHIPVFGSIAKEPPMHIVHIAVEMAPIAKVGGLGDVVTSLSRAVQDLGHNVEVILPKY 1269
SS3  DYHIPVFGGVAKEPPMHIVHIAVEMAPIAKVGGLGDVVTSLSRAVQDLNHNVDILPKY  823

DU1  GCLNLSNVKNLQIHQSFSWGGSEINVWRGLVEGIQVYFLEPQNGMFGVGMVYGRDDR   1328
SS3  DCLKMNNVKDFRFHKNYFWGGIELKVWFGKVEGISVYFLEPQNGLSKGQVYGCSNDGE  882
```

FIGURE 6A-2

```
DU1  RFGFFCR SALEFLLQS GSSPN IIHCHDWSSAPVAWLHKEN YAKSSLANAR VFTIHNLE       1387
SS3  RFGFFCH AALEFLLQQ GFSPD IIHCHDWSSAPVAWLFKEQ YTHYGLSKSR IVFTIHNLE        941

DU1  FGAHHIGK AMRYCDKATTVSN TYSKEVSGHGA IMPHIGKFYGI LNGIDPDIWDP YNDNF      1446
SS3  FGADLIGR AMTNADKATTVSP TYSQEVSGNPV IAPHIHKFHGI VNGIDPDIWDE LNDKE      1000

DU1  IPVHYIC ENVVEGKR AAKRALQQ KFGLQQ IDMPVGI VTRLTAQ KGIHLIKHA IHRTLE     1505
SS3  IPIPYIS ENVVEGKT AAKFALQ RKIGLRQAD IPLVGIIITRLTHQ KGIHLIKHAI WRTLE    1059
                                                                    II

DU1  RNGQVVLLGSAPDSRHQA DFVNLANIL HGVNHGQVRL SLTYDEPLSHLIYAGS DFILVP       1564
SS3  RNGQVVLLGSAPDPRVQN FVNLANQLH SKYNDRARLC LTYDEPLSHLIYAGA DFILVP        1118
                II

DU1  SIFEPCGLTQL VAMRYGHI PTVRKTGGL FDTVFDVNDKERA RDRGLEPNGFSFDGADS        1623
SS3  SIFEPCGLTQLF AMRYGSI PMVRKTGGI MDTVFDVDHDKERA QQCGLEPNGFSFDGADA       1177

DU1  NGVDYALNRAI SAWFDARSWFH SLCKR VMEQDWSNRPALDY ELYRSASKL                1674
SS3  GVDYALNRAL SAWDGRDWFN SLCKV MEQDWSNRPALDY ELYHAARKLE                  1230
```

DU1    (SEQ ID NO: 12)

SS3    (SEQ ID NO: 35)

FIGURE 6A-3

SBE-repeats in DU1:

| | | | |
|---|---|---|---|
| 478 | DQSIVG SHKQ | 487 | (SEQ ID NO: 16) |
| 538 | DQSIVG SLKQ | 547 | (SEQ ID NO: 17) |

↑ 6/6 match

| | | | |
|---|---|---|---|
| 448 | NQSIVG SCKQ | 457 | (SEQ ID NO: 18) |
| 568 | NQSIVG LPKQ | 577 | (SEQ ID NO: 19) |
| 418 | DQSIAG SHRQ | 427 | (SEQ ID NO: 20) |
| 428 | DQSIAG APEQ | 437 | (SEQ ID NO: 21) |
| 404 | DKSIVG VPQQ | 413 | (SEQ ID NO: 22) |
| 598 | DLSIVG NEFQ | 607 | (SEQ ID NO: 23) |

↑ 5/6 match

FIGURE 7B-1

SBEI family:

```
         529                     *              *                        553
Maize SBEI     KCIAYAESH    DQSIVG    DKTIAFLLMD        (SEQ ID NO: 24)
Pea SBEI       KCVSYAESH    DQSIVG    DKTIAFLLMD        (SEQ ID NO: 25)
Wheat SBEI     KCIAYAESH    DQSIVG    DKTMAFLLMD        (SEQ ID NO: 26)
                                         ←—— 6/6 match ——→
```

SBEII family:

```
         572                     *              *                        596
Maize SBEIIa   KCVTYCESH    DQALVG    DKTIAFWLMD        (SEQ ID NO: 27)
Maize SBEIIb   KCVTYAESH    DQALVG    DKTIAFWLMD        (SEQ ID NO: 28)
Pea SBEI       KCVVYCESH    DQALVG    DKTLAFWLMD        (SEQ ID NO: 29)
                                         ←—— 4/6 match ——→
```

Glycogen branching enzymes:

```
         477                     *              *                        501
Yeast GLC3     KVVAYCESH    DQALVG    DKSLAFWLMD        (SEQ ID NO: 30)
Human liver    KCIAYAESH    DQALVG    DKTLAFWLMD        (SEQ ID NO: 31)
                                         ←—— 4/6 match ——→
```

FIGURE 7B-2

150 → ETVDEAEVEEDK--FEVDTSGIVLRNVAVR    (SEQ ID NO: 32)
      E-VDPKDEHNAKDVFVVDSSGTAPDNAAVE    (SEQ ID NO: 33)
      EVVDEAEVEEDM--VDVDILGLDLNNATI ← 233 (SEQ ID NO: 34)

FIGURE 7C

DULL1 CODING FOR A NOVEL STARCH SYNTHASE AND USES THEREOF

FEDERAL FUNDING LEGEND

This invention was produced in part using funds under USDA Grant number 96-35300-3779. Consequently, the federal government has certain rights in this invention.

BACKGROUND OF THE INVENTION

1. Field of the Invention

The present invention relates generally to carbohydrate biochemistry. More specifically, the present invention relates to starch biosynthesis and the enzyme(s) involved.

2. Description of the Related Art

Starch, the most significant carbohydrate reserve in plant storage tissues, comprises the glucose homopolymers amylose and amylopectin. Amylose consists of predominantly linear chains of α-(1→4)-linked glucose residues, whereas amylopectin is a highly branched glucan with a specific "clustered" distribution of α-(1→6) glycosidic bonds (i.e branch linkages) connecting linear chains French, 1984; Manners, 1989).

Despite the relatively simple chemical structure of amylopectin, very little is known about the enzymatic processes responsible for formation of the highly specific and complex branching patterns in this polysaccharide. Biosynthesis of amylose and amylopectin involves activities of four groups of enzymes, each of which comprises multiple isozymes. These enzymes are ADPG pyrophosphorylases (AGPase), starch synthases (SS), starch branching enzymes (SBE) and starch debranching enzymes (SDBE) (Preiss, 1991; Hannah et al., 1993; Martin and Smith, 1995; Nelson and Pan, 1995; Ball et al., 1996; Preiss and Sivak, 1996; Smith et al., 1996). These enzymatic steps can account for all chemical linkages in starch, however, the specific roles of individual isozymes in formation of specific branching patterns in amylopectin and determination of starch granule structure and properties remain unknown.

Analysis of maize mutants with abnormal endosperm phenotypes has contributed greatly to the understanding of starch synthesis (Shannon and Garwood, 1984; Nelson and Pan, 1995) and facilitated the identification of many genes coding for starch biosynthetic enzymes. Cloned genes whose products are thought to be involved directly in starch biosynthesis are waxy (wx), coding for the granule-bound starch synthase GBSSI (Shure et al., 1983; Klösgen et al., 1986), amylose extender (ae), coding for SBEIIb (Fisher et al., 1993; Stinard et al., 1993), shrunken2 (sh2) and brittle2 (bt2), coding for the large and small subunits of AGPase, respectively (Bae et al., 1990; Bhave et al., 1990), and sugary1 (su1), coding for the SDBE SU1 (James et al., 1995). The transposon-tagging strategy was used to determine that the abnormal endosperm phenotype of wx-, ae-, or su1- mutants results from primary defects in GBSSI, SBEIIb, or SU1, respectively, and this approach remains the most effective way to identify genes such as dull1 (du1), in which the primary defect can not be associated with a particular enzyme deficiency.

The du1- mutations define a gene with a very important function in starch synthesis, as indicated by extensive structural analyses of starch from du1- mutant endosperms, and by the effects of these mutations when combined with other genetic deficiencies in starch biosynthetic enzymes (Shannon and Garwood, 1984; Nelson and Pan, 1995). The reference mutation du1-Ref was first identified as a recessive modifier of su1-Ref and su1-amylaceous (su1-am) (Mangelsdorf, 1947). Mutations of du1, when homozygous in otherwise non-mutant backgrounds, result in mature kernels with a tarnished, glassy, and somewhat dull appearance referred to as the "dull phenotype". Expression of this phenotype, however, depends on the particular genetic background (Mangelsdorf, 1947; Davis et al., 1955). Total carbohydrate and starch content in mature du1-mutant kernels is slightly lower than normal (Creech, 1965; Creech and MeArdle, 1966). The apparent amylose content in starch from du1- mutants is slightly or greatly elevated compared to normal depending on the genetic background (Shannon and Garwood, 1984), although the properties of polysaccharides in the apparent amylose fraction are essentially not altered (Dvonch et al., 1951). Approximately 15% of the starch in du1- mutant endosperms is in a form known as "intermediate material", which is distinguished from amylose and amylopectin by the properties of its starch-iodine complex (Wang et al., 1993b). Analysis of combined amylopectin/intermediate material fractions indicated that starch from du1- mutants has the highest degree of branching among a wide variety of normal and mutant kernels analyzed (Inouchi et al., 1987; Wang et al., 1993a; Wang et al., 1993b). Starch granules from du1- mutants seem to have normal structural and physical properties, although some abnormally shaped granules are found in the mutant endosperm (Shannon and Garwood, 1984).

Despite these subtle effects exerted by the single mutation, du1-alleles when combined with other mutations affecting starch synthesis result in a broad range of more severe alterations (Shannon and Garwood, 1984; Nelson and Pan, 1995). Mutations of du1 have been examined in combination with wx-, ae-, su1-, and sugary2 (su2-) mutations, and in all instances the double mutant kernels contained more soluble sugars and less total starch than when any of the mutations was present alone. In many instances the double mutants also produce polysaccharide forms that are distinct from the starch found in any single mutant kernels. These pleiotropic effects indicate the product of Du1 affects many aspects of starch biosynthesis in maize endosperm, however, without knowing the identity of this protein it is difficult to assess its specific functions.

Consistent with the pleiotropic genetic effects, du1-mutations cause reduced activity in endosperm of two seemingly unrelated starch biosynthetic enzymes, the starch synthase SSII and the branching enzyme SBEIIa (Boyer and Preiss, 1981). SSII is one of two enzymatically distinct starch synthase activities identified in the soluble fraction of maize endosperm; in vitro activity of SSII requires an exogenous glucan primer, and its molecular weight was determined in different studies as either 95 kD or 180 kD (Boyer and Preiss, 1981; Mu et al., 1994). Similarly, SBEIIa is one of the three known SBE isozymes in endosperm cells (Boyer and Preiss, 1978b; Fisher et al., 1993; Fisher et al., 1995; Gao et al., 1997). Several possibilities exist to explain the dual biochemical effects of du1- mutations. Du1 may code for a protein regulating the expression or activity of both SSII and SBEIIa. Alternatively, Du1 may code for either of these two enzymes, and the deficiency in one enzyme might also affect the second enzyme because of a direct or substrate-mediated physical interaction.

DU1 codes for a starch synthase, as indicated by the extensive similarity of its deduced amino acid sequence to potato SSIII, and by the substantial similarity between the C-terminal residues of DU1 and a large group of phylogenetically diverse starch- and glycogen synthases. Particularly striking are two regions that together comprise more than half of the deduced DU1 sequence of 1,674 residues, which share very high similarity of 51% and 73%, respectively, with the corresponding regions of the potato SSIII sequence. Within a stretch of 450 amino acids at the C-terminus of DU1 nearly 30% of the best aligned residues are identical in comparisons to a wide variety of starch- and glycogen synthases, suggesting the location of a domain within DU1 that provides α-1,4-glycosyltransferase acitivity.

The starch synthase coded for by Du1 is the soluble isozyme identified biochemically as SSII (Ozbun et al., 1971; Boyer and Preiss, 1981). The deduced molecular weight of Du1 including a potential transit peptide, 188 kD, matches closely with that of 180 kD reported for mature SSII lacking a transit peptide (Mu et al., 1994). The size difference of approximate 8 kD may be due to the transit peptide present in the deduced DU1 sequence. The tissue specific expression pattern of the Du1 mRNA also matches the expression pattern of SSII. Du1 transcripts were undetectable in leaves either by RNA gel blot or RT-PCR analyses, corresponding with that fact no detectable SSII activity was present in leaf extracts (Dang and Boyer, 1988). Moreover, the activity of SSII, along with that of SBEIIa, was greatly reduced in du1-mutant endosperm (Boyer and Preiss, 1981). Therefore, it appears that the maize du1 locus codes for the soluble starch synthase SSII, the counterpart of potato SSIII.

This characterization of Du1 implies that the phenotypic effects of du1- mutations, including changes in starch structure, deficiencies of two starch biosynthetic enzymes, and genetic interactions with ae-, su1-, su2-, and wx- mutations, all result either directly or indirectly from alteration of SSII. The reduction of SBEIIa activity in du1-mutant endosperm could result from the SSII deficiency owing to physical interaction between the two enzymes. A direct physical association of SSII and SBEIIa is implied by the observation that peak activities of both SSII and SBEIIa always coincide in the same DEAE-cellulose column fractions (Boyer and Preiss, 1978a; Boyer and Preiss, 1981; Dang and Boyer, 1988). Thus, SSII and SBEIIa may function together in vivo in the form of single multi-enzyme complex. Loss of the intact enzyme complex owing to reduction of SSII in du1-mutant endosperm may result in abnormally rapid proteolytic turnover of SBEIIa, or prevent accumulation of the enzyme by some other mechanism. Alternatively, expression of the Sbe2a gene in du1 -mutant endosperm may be inhibited as a more indirect consequence of the deficiency in SSII, for example through reduction of a transcriptional inducer or elevation of a repressor. Although the du1-Ref mutation does indirectly affect expression of other starch biosynthetic genes (Giroux et al., 1994), it actually caused increased gene expression rather than the reduction observed for SBEIIa. Furthermore, considering that large glucose polymers are expected to be the substrate and product of DUI, down-regulation of Sbe2b expression by a transcriptional mechanism seems unlikely. Thus, the former hypothesis may explain the deficiency of SBEIIa in du1-mutant endosperm.

The broad impact of the combination of du1- mutations with various su1-alleles on kernel phenotype and starch synthesis (Cameron, 1947; Shannon and Garwood, 1984) could be explained by the SU1 SDBE also interacting closely with SSII in vivo, perhaps in the same enzyme complex with SBEIIa. This proposed association of SBEIIa and SU1 in a multi-enzyme complex is consistent with the proposed simultaneous branching and debranching actions during amylopectin synthesis by SBE and SDBE (James et al., 1995; Nelson and Pan, 1995; Ball et al., 1996).

Thus, the prior art is deficient in understanding the complex association of enzymes involved in starch synthesis and in cloning genes corresponding to these enzymes. The present invention fulfills this long-standing need and desire in the art.

SUMMARY OF THE INVENTION

To illustrate the role of the du1 locus in starch biosynthesis, a transposon-tagging strategy was used to isolate the gene and describe its polypeptide product. The present invention reports tagging of the du1-locus with a Mutator (Mu) transposon, cloning and characterization of a portion of the gene, and the sequence of a near full-length cDNA (SEQ ID No. 1). The amino acid sequence deduced from this cDNA indicates Du1 codes for a 186 kD polypeptide extremely similar to SSIII, a starch synthase from potato tubers (Abel et al., 1996; Marshall et al., 1996). The expression pattern of Du1 also was characterized. Taken together these characterizations indicate that Du1 most likely codes for SSII of maize endosperm. In addition, the product of Du1 contains unique sequence features in its amino terminus that may mediate direct interactions with other starch biosynthetic enzymes.

One object of the present invention is to provide an enzyme with which to regulate the production of starch, and with which to produce altered or novel forms of starch.

In an embodiment of the present invention, there is provided a cDNA corresponding to the dull1 gene of maize.

In yet another embodiment of the present invention, there is provided an expression vector containing the sequence of dull1 with which to produce the starch synthase enzyme in transgenic plants or other prokaryotic or eukaryotic organism.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1 shows the isolation of du1- mutations.

FIG. 2 shows a Mu1-containing BamHI Genomic DNA Fragment Cosegregates with du1-R2370::Mu1.

FIG. 3 shows the isolation of a near full-length Du1 cDNA clone.

FIG. 5 shows the Du1 gene has a unique expression pattern.

FIG. 6 shows the DU1 amino acid sequence is most similar to that of potato SSIII. FIG. 6A shows the primary sequence alignment. The deduced amino acid sequences of DU1 and potato SSIII (GenBank accession number X95759) are aligned. Solid directional arrows indicate the positions of the three 60 amino acid SBE-superrepeats, and dotted arrows denote individual copies of the SBE-repeat. Dashed arrows indicate the positions of the three repeat units that make up the 85 residue repeat. Double-headed arrows labeled with Roman numerals indicate the positions of correspondingly designated conserved sequence blocks identified in the glucan synthase family (Preiss and Sivak, 1996).

FIG. 7 shows the repeats in the unique DU1 amino terminus. FIG. 7B shows the alignment of selected copies of the SBE-repeat and conservation of the M-box within branching enzymes. In the first grouping numbers refer to position within the DU1 coding sequence. Boxed residues are identical to the consensus sequence of the SBE-repeat. Arrows indicate the M-box sequence (DQSIVG). The M-box sequence is almost completely conserved in the members of SBEI family, including maize SBEI (GenBank accession no. D11081), pea SBEII (GenBank accession no. X80010), wheat SBEI (GenBank accession no. Y12320). The M-box sequence is also well conserved, with substitution of two residues of similar properties, in members of the SBEII family and glycogen synthases, including maize SBEIIa (Gao et al., 1997), maize SBEIIb (GenBank accession no. L08065), pea SBEI (GenBank accession no. X80009), glycogen synthase from human liver (GenBank accession no. D29685) and *S. cerevisiae* glycogen synthase (the GLC3 product; GenBank accession no. M76739). Residue numbers refer to the first enzyme in each group. Arrows indicate the occurrence of M-box sequences or related sequences. Asterisks indicate conserved residues that in amylolytic enzymes of determined structure are known to be part of the active site. FIG. 7C shows the sequence conservation of the 28 amino acid repeat. The three repeats within the 85 residue repeat region were best aligned to show the pattern of sequence conservation among the two portions of the 28 residue basic repeating unit. Numbers refer to positions within the DU1 coding sequence.

DETAILED DESCRIPTION OF THE INVENTION

Figure 1A:
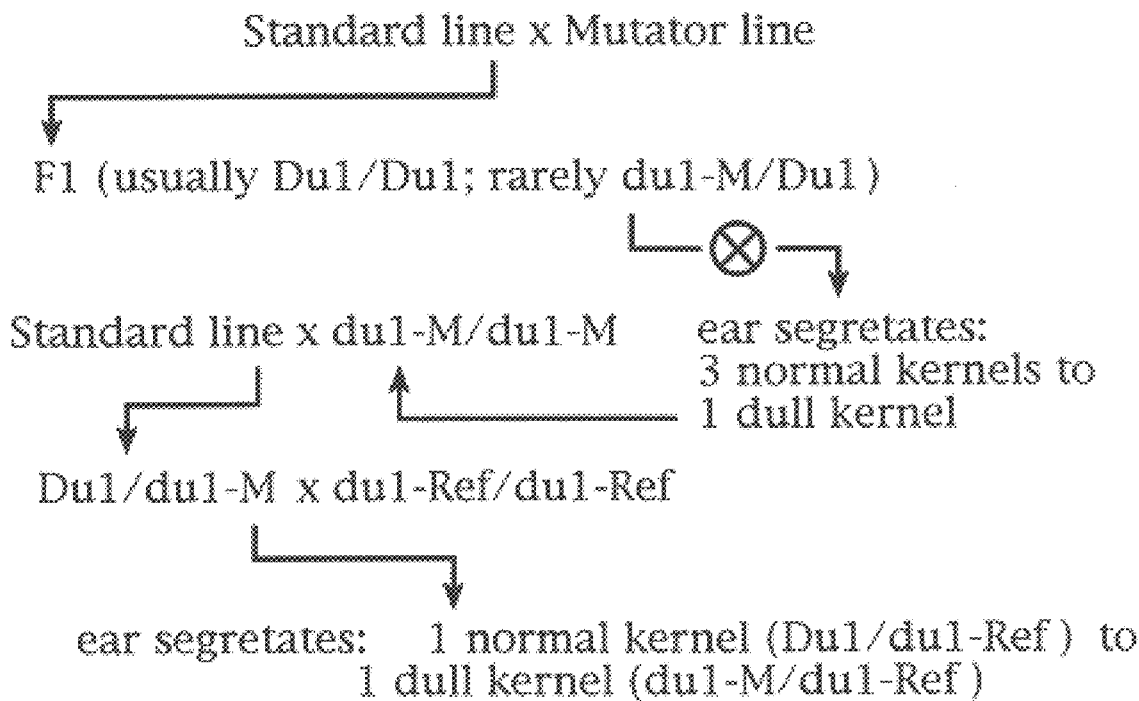
FIG. 1A shows the crossing scheme. The specific maize lines used in this procedure are listed below. The allele designation "du1-M" indicates a putative recessive mutation in the du1 locus caused by insertion of a Mu transposon.

In accordance with the present invention there may be employed conventional molecular biology, microbiology, and recombinant DNA techniques within the skill of the art.

Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can up regulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene which encodes a maize starch synthase enzyme of the present invention can be used to transform a host using any of the techniques commonly known to those of ordinary skill in the art. One preferred embodiment is the use of a vectors containing coding sequences for the gene which encodes a maize starch synthase enzyme of the present invention for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

In addition, the invention also includes fragments (e.g., antigenic fragments or enzymatically functional fragments) of the maize starch synthase enzyme. As used herein, "fragment," as applied to a polypeptide, will ordinarily be at least 10 residues, more typically at least 20 residues, and preferably at least 30 (e.g., 50) residues in length, but less than the entire, intact sequence. Fragments of the starch synthase enzyme can be generated by methods known to those skilled in the art, e.g., by enzymatic digestion of naturally occurring or recombinant starch synthase protein, by recombinant DNA techniques using an expression vector that encodes a defined fragment of starch synthase, or by chemical synthesis. The ability of a candidate fragment to exhibit a characteristic of starch synthase (e.g., binding to an antibody specific for starch synthase, or exhibiting partial enzymatic or catalytic activity) can be assessed by methods described herein. Purified fragments of starch synthase or antigenic fragments of starch synthase can be used to generate new starch regulatory enzyme using multiple functional fragments from different enzymes, as well as to generate antibodies, by employing standard protocols known to those skilled in the art.

A standard Northern blot assay can be used to ascertain the relative amounts of starch synthase mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of the starch synthase gene in transgenic systems, in accordance with conventional Southern hybridization techniques known to those of ordinary skill in the art. Both the Northern blot and Southern blot use a hybridization probe, e.g. radiolabelled maize starch synthase cDNA, either containing the full-length, single stranded DNA having a sequence complementary to SEQ ID No. 1 or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, b-glucuronidase, b-D-glucosidase, b-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "metabolism" is defined as the sequence of enzyme-catalyzed reactions in which a molecule is either degraded to more simple products, or synthesized from simple precursors.

The present invention is directed towards a cDNA corresponding to the gene encoding the maize starch synthase enzyme. That is, the present invention provides an isolated cDNA having the sequence shown in SEQ ID No. 1 encoding a starch synthase II enzyme from maize. The present invention is also directed to an expression vector comprising this cDNA operably linked to a promoter allowing expression of this cDNA. Such an expression vector can be used to transfect a host cell to produce desired quantities of the maize starch synthase enzyme.

The present invention is also directed to a starch synthase II protein or fragments or derivatives thereof, wherein the protein has a molecular weight of approximately 180 kDA, maximal transcript level in endosperm at 12 days after pollination, a C-terminal region possessing α-1,4-glycosyltransferase catalytic activity, and an N-terminal region containing the amyloplast targeting peptide and repeat motifs comprising, but not limited to, the M-box (SEQ ID No. 9).

In another embodiment, the present invention also provides for an antibody directed towards the maize starch synthase polypeptide, or functional fragments thereof.

In yet another embodiment, the present invention is directed towards a transgenic plant, wherein the transgene is an expression vector comprising the cDNA corresponding to the maize starch synthase gene.

In another aspect, the present invention is directed to a method of producing starch, comprising the steps of transforming a cell with the vector described herein, and extracting and purifying said starch using methods described in the instant specification and readily known to one of skill in the art. This method can be used in conjunction with cells that carry additional mutations in genes involved in starch synthesis and/or metabolism, glucose sythesis and/or metabolism, glycogen sythesis and/or metabolism, and carbohydrate synthesis and/or metabolism.

The following examples are given for the purpose of illustrating various embodiments of the invention and are not meant to limit the present invention in any fashion:

EXAMPLE 1

Nomenclature, Plant Materials and Isolation of du1- Mutations

Nomenclature follows the standard maize genetics format (Beavis et al., 1995). Alleles beginning with a capital letter indicate a functional, i.e. non-mutant, form of the gene (e.g. Du1). Unspecified mutant alleles are indicated by dashes with no following designation (e.g. du1-). Gene products are indicated by non-italicized upper-case letters (e.g. DU1). Transcripts and cDNAs are indicated by the non-italicized gene symbol (e.g. Du1).

Standard lines used were the F1 hybrids B77/B79 or Q66/67, products of four inbred lines that have no history of Mutator activity. The Mu-active parents used in the mutant isolation scheme were described by Roberston (1978). Maize inbred line W64A was used for detection of the Du1 transcript in kernels and other tissues.

Mutant alleles du1-R2197, du1-R2339, du1-R2649, du1-R2370::Mu1, du1-R4059, and du1R-1178 were identified from the ears of self-pollinated F1 plants 87-2197-9, 87-2339-2, 87-88-2649-11, 87-2370-20, 82-4059-23, 89-1178-3, respectively (FIG. 1A). Inclusion of the letter R in the allele names indicates the stocks originally are from the laboratory of Dr. D. S. Robertson, and inclusion of the term Mu1 in allele name du1-R2370::Mu1 indicates this transposon has been identified definitively within the mutant gene. Stock number X10A from the Maize Genetics Cooperation Stock Center (Urbana, Ill.), homozygous for the reference allele du1-Ref, was used for complementation tests and to generate segregating populations (FIG. 1A).

EXAMPLE 2

Cloning

The methods used for genomic DNA extraction and DNA gel blot analysis were as described (James et al., 1995). Most probes were $^{32}$P-labeled by the standard random-primed method (Boehringer Mannheim, Indianapolis Ind.). The 2.0 kb BamHI fragment that contains Mu1 and cosegregates with du1-R2370::Mu1 was isolated from a size-selected λZAPII-express library constructed from BamHI-digested genomic DNA from a du1-R2370::Mu1/du1-Ref plant essentially as described (James et al., 1995), and subcloned in pBluescript SK+ to form plasmid pJW3. Fragment F500 (FIG. 2B) was amplified for use as a probe by PCR from pJW3 using primers du1-sp1 (5'-GTACAATGACAACTTTATCCC-3') (SEQ ID No. 2) and du1-sp2 (5'-CATTCTCACAAG-TGTAGTGGACC-3') (SEQ ID No. 3). The single-stranded, $^{32}$P-labeled, F500 probe was generated by PCR using primer du-sp1 and the gel-purified BamHI fragment from pJW3 as a template according to Konat et al. (1994).

For PCR amplification of a longer genomic fragment overlapping the sequence flanking the Mu1 element in the 2.0 kb BamHI fragment, size-selected fragments were prepared from 80 μg of EcoRI-digested genomic DNA of sibling wild type plants (Du1/du1-Ref, see FIG. 1A) fractionated on a 0.5% preparative agarose gel. Five fractions of EcoRI fragments were isolated by electroelution (Sambrook et al., 1989) from consecutive gel slices bracketing the 6.0 kb size marker, and checked for the presence of Mu1-flanking sequences in the original cloned BamHI fragment by PCR using primers du1-sp1 and du1-sp2. Aliquots of two fractions containing the highest amounts of the target fragment were ligated to EcoRI-linearized pBluescript SK+, and 1 μl of each ligation mixture was used directly for PCR amplification of the region overlapping the cloned BamHI fragment using primer du1-sp1 or du1-sp2 in pairwise combination with primer T3 or T7 in pBluescript SK+. A fragment of about 2.0 kb amplified by the primer pair du1-sp1 and T3 was confirmed to contain the BamHI fragment by subsequent PCR amplification using primers du1-sp1 and du1-sp2, and was used as template for another round of PCR using the nested primer du1-sp4 (FIG. 3A) (5'-GTCGTAGGAATCGTCACTCG-3') (SEQ ID No. 4) and primer T3. The specifically amplified 1.3 kb fragment was polished with T4 DNA polymerase, digested with EcoRI to remove the remaining vector sequence, and then cloned into the EcoRV and EcoRI sites of pBluescript SK+ to form plasmid pMg1A.

EXAMPLE 3 cDNA Library Screen

Random-primed maize endosperm cDNA libraries in λgt11 were provided by Dr. Karen Cone (University of Missouri, Columbia, Mo.). Standard procedures were followed for preparation of phage lifts, phage amplification, and single-plaque purification (Ausubel et al., 1989; Sambrook et al., 1989). Phage lifts were hybridized at 65° C. for 16–18 hours to probes labeled with $^{32}$P-dCTP by the random-primed method and washed under high stringency conditions as described by Church and Gilbert (1984). cDNA inserts in phage clones were subcloned in pBluescript SK+ or pBluescript KS+ from phage DNAs prepared by the Wizard DNA purification kit (Promega).

cDNA inserts in purified phage were characterized regarding their length by direct PCR amplification from disrupted phage using two primers, λ1030 (5'-ATTGGTGGCGACGA-CTCCTG-3') (SEQ ID No. 5) and λ1356 (5'-GTGTGGGGGTGATGGCTTCC-3') (SEQ ID No. 6), located 19 bp proximal to the EcoRI cloning site in the left arm and 281 bp distal to EcoRI site in the LacZ' region of the right arm in λgt11 phage DNA, respectively. An aliquot of homogeneous purified phage (1 µl of a 1×10$^{10}$ pfu/µl phage suspension) was disrupted in 20 µl of optimal PCR buffer (10 mM Tris-HCl, pH 9.2, 1.5 mM MgCl$_2$, 25 mM KCl) containing 0.2 µM each of the two primers and 0.2 mM each of four dNTPs for 15–20 min at 96° C., and then directly used for PCR amplification of the cDNA inserts typically as follows: 94° C. for 4 min, one cycle (add 1 unit Taq DNA Polymerase at the end); 10 cycles of 58° C. for 45 sec, 72° C. for 0.5 to 3 min (depending on the insert size) and 94° C. for 45 sec; 20 cycles of 61° C. for 1 min, 72° C. for 0.5 to 3 min (depending on the insert size) and 94° C. for 1 min; and 1 cycle of 61° C. for 5 min and 72° C. for 7 min. Lengths of cDNA inserts were determined by gel electrophoresis of 5–10 µl of the PCR products.

The CDNA library screening was as follows. In the first round, about 340 positive signals were obtained in primary screening of approximately 0.5×10$^6$ pfu using fragment BE1300 as a probe. The longest cDNA insert among 15 further purified and characterized clones was 3.2 kb in length (nt 2577 to nt 5782 in the near full-length sequence). This insert was subcloned as two EcoRI fragments in plasmids pMg271L and pMg271S containing the 2.7 kb cDNA at the 5' end and the 0.5 kb cDNA at the 3' end, respectively. In the second round, the 0.5 kb EcoRI/ScaI fragment at the extreme 5' end of the 2.7 kb cDNA insert in pMg271L and the 0.5 kb EcoRI fragment of pMg271S were used separately as probes in the primary screening of an additional 1.5×10$^6$ pfu of phage. The longest insert identified by the 5' end probe in one of 24 purified and characterized phage clones, 4.3 kb in length, was subcloned in plasmid pMg6Aa. The probe from pMg271S identified an approximately 4.0 kb cDNA insert containing a 3' end EcoRI fragment of 0.67 kb that overlapped with and extended the original cloned 3' end fragment. The 1.4 kb portion from the 3' end of this 4.0 kb cDNA insert was amplified by PCR directly from purified phage and cloned as a BamHI/HindIII fragment in pMgt6-2M. The original terminal EcoRI site was mutated to a HindIII site during PCR amplification to facilitate subsequent reconstruction of the complete cDNA. The BamHI fragment of 240 bp at the 5' end of the cDNA in pMg6Aa was then used as a probe for the primary screening of another 1.0×10$^6$ pfu in the third round. Among 19 purified and characterized phage clones, the CDNA insert that overlapped with the insert in pMg6Aa and containing the longest extension at the 5' end, about 1.5 kb in length, was subcloned in plasmid pMgf10. The continuous sequence of three overlapping cDNA fragments in plasmids pMgf10, pMg6Aa, and pMgt6-2M represents the near full-length cDNA sequence (FIG. 3B). Nucleotide sequences were obtained using ABI Prism automated sequencing system (Perkin Elmer) at the Iowa State University Nucleic Acid Sequencing and Synthesis Facility, using double-stranded plasmid templates. All nucleotide sequences were confirmed by analysis of both strands. Computational analyses were performed using the Wisconsin Package (Genetics Computer Group, Madison, Wis.) and the Lasergene software package (DNASTAR Inc., Madison, Wis.).

EXAMPLE 4

RNA Gel Blot Analysis and RT-PCR

Extraction of total RNA from various tissues of maize inbred W64A and RNA gel blot analysis were essentially as described (Gao et al., 1996). Radioactivity of transcripts hybridized to the Du1 cDNA probe was analyzed and quantified using a Phosphorimager (Molecular Dynamics, Sunnyvale, Calif.), and expressed as the percentage of the maximal signal strength on the same blot (Relative Level or R.L %). Minor loading differences among samples on each blot were calibrated using a tomato cDNA probe hybridizing to the 26S rRNA in the appropriate lane to normalize the Du1 mRNA signal strength.

The RT-PCR assay utilized the Titan RT-PCR system (Boehringer Mannheim) following manufacturer's instruction. The two primers used were du1-F3 (5'-ATAAATGTGTGGCGT-GGACT-3') (SEQ ID No. 7) and du-R1 (5'-CGTTCCTTGTCATTGTCCAC-3') (SEQ ID No. 8) spanning the 934 bp cDNA region from nt 3997 to nt 4930. Total RNA (1 µg) from various samples were used as templates. To distinguish RT-PCR amplification of mRNA from PCR amplification of potential residual genomic DNA, total RNA from one of the samples (22 DAP endosperm) was treated with RNase A (100 ng/ml) for 10 min at 37° C. prior to its use as a template. The RT-PCR products were analyzed on a 1% agarose gel, then blotted and hybridized using the cDNA insert of pMg6Aa as the probe to confirm the identity of the product.

EXAMPLE 5

Identification of du1- Mutations

Figure 1B:
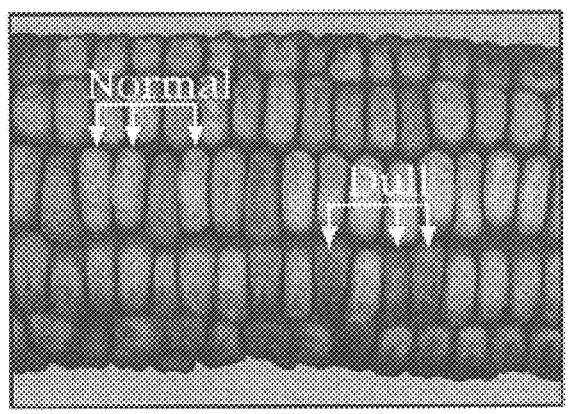
FIG. 1B shows the dull mutant phenotype. The ear shown was obtained by self-pollination of a du1-R2370::Mu1/Du1 heterozygote. Dull kernels and wild type kernels are present at approximately the Mendelian frequency of 1:3, respectively.

Novel du1- mutations were identified in plants derived from parental lines containing an active Mu transposable element system by the strategy outlined in FIG. 1A. Standard non-Mu lines were pollinated by Mu-active plants, and the resultant F1 progeny were self-pollinated. Six F1 ears were found that contained kernels with the dull phenotype at a frequency of approximately 25%, as illustrated in FIG. 1B. Plants grown from the dull kernels were crossed to standard lines to generate presumed Du1/du1 heterozygous kernels. These were grown to maturity and crossed to du1-Ref/du1-Ref tester plants, resulting in a 1:1 segregating population of dull and normal sibling kernels for each of the six putative Mu-induced du1- alleles. Thus, in all instances the dull phenotype is a single gene trait conditioned by a mutation that most likely is allelic to du1-Ref. The novel du1- mutations are termed du1-R2370::Mu1, du1-R2339, du1-R2649, du1-R4059, du1-R2197, and du1-R1178.

EXAMPLE 6

Cloning and Characterization of the du1- Genomic Loci

Figure 2A:
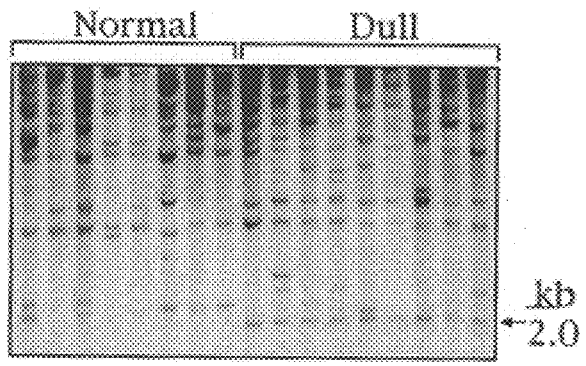
FIG. 2A shows detection of Mu1-containing genomic DNA fragments. BamHI-digested genomic DNA of seedlings grown from segregating (1:1) non-mutant and dull sibling kernels was separated on a 1% agarose gel, blotted, and probed with the 960 bp internal MluI fragment of Mu1 excised from plasmid pMJ9 (Barker et al., 1984).

A specific Mu1 transposon was found to cosegregate with the dull phenotype among progeny of a du1-R2370::Mu1/Du1 heterozygote. The heterozygous parent was crossed to a du1-Ref homozygote, generating ears containing approximately 50% dull kernels (du1-R2370::Mu1/du1-Ref) and 50% normal kernels (Du1/du1-Ref). Genomic DNAs were extracted from seedlings germinated from 35 kernels of each type, digested with BamHI, and subjected to gel blot analysis using the 960 bp internal MluI fragment of Mu1 as a probe. FIG. 2A shows representative data from these analyses; a 2.0 kb Mu1-containing fragment was detected in all analyzed plants bearing du1-R2370::Mu1, but not in any plants lacking this allele.

Figure 2B:
FIG. 2B shows the structure of the cloned 2.0-kb BamHI fragment. The hatched bar indicates the position of Mu1 as revealed by the nucleotide sequence of the cloned fragment. The position of the 500 bp probe fragment F500 is indicated, and the figure is drawn to scale. Restriction sites are indicated for BamHI (B) and NotI (N).
Figure 2C:
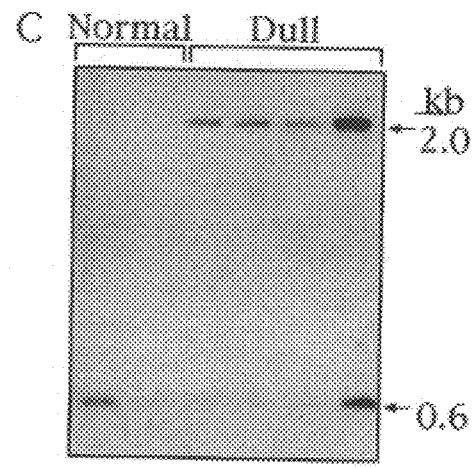
FIG. 2C shows detection in genomic DNA of restriction fragments homologous to the cloned fragment. The analysis is the same as that shown in FIG. 2A, except that the blot was hybridized with a single-stranded probe generated by PCR using fragment F500 shown in FIG. 2B as the template.

The 2.0 kb Mu1-containing genomic DNA fragment that cosegregated with the dull mutant phenotype was cloned by screening a size-fractionated genomic library, prepared from a du1-R2370::Mu1/du1-Ref heterozygote in the vector λZAPII-express, using an internal fragment of Mu1 as a probe. FIG. 2B shows the structure of the cloned fragment. As expected, the nucleotide sequence of this fragment revealed two 9 bp direct repeats (5'-GTGAGAATG-3') flanking a Mu1 element. FIG. 2C illustrates a subsequent DNA gel blot analysis confirming that the cloned Mu1-containing fragment was derived from the genomic interval that cosegregates with du1-R2370::Mu1. The single stranded probe F500, which is adjacent to the Mu1 element (FIG. 2B), detected a fragment of approximately 0.62 kb in all plants of the segregating population, and also a fragment of approximately 2.0 kb specific to plants derived from dull kernels (du1-2370::Mu1/du1-Ref). In all, 27 kernels of each type were characterized. The 1.4 kb size difference indicates that the larger 2.0 kb BamHI fragment most likely arose from insertion of a 1.4 kb Mu1 element within the 0.62 kb region delineated by these two BamHI sites. Taken together these data indicate that the cloned Mu1-containing fragment either is located within the du1 locus or is closely linked to it.

Figure 3A:
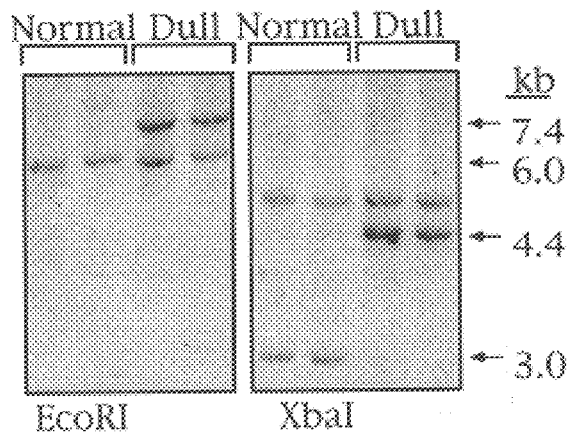
FIG. 3A shows the identification of genomic fragments containing regions flanking the Mu1 element in the cloned 2.0 kb BamHI fragment. EcoRI- and XbaI-digested genomic DNA from du1-R2370::Mu1/du1-Ref mutants and sibling Du1/du1-Ref non-mutant seedlings was probed with fragment F500.
Figure 3B:
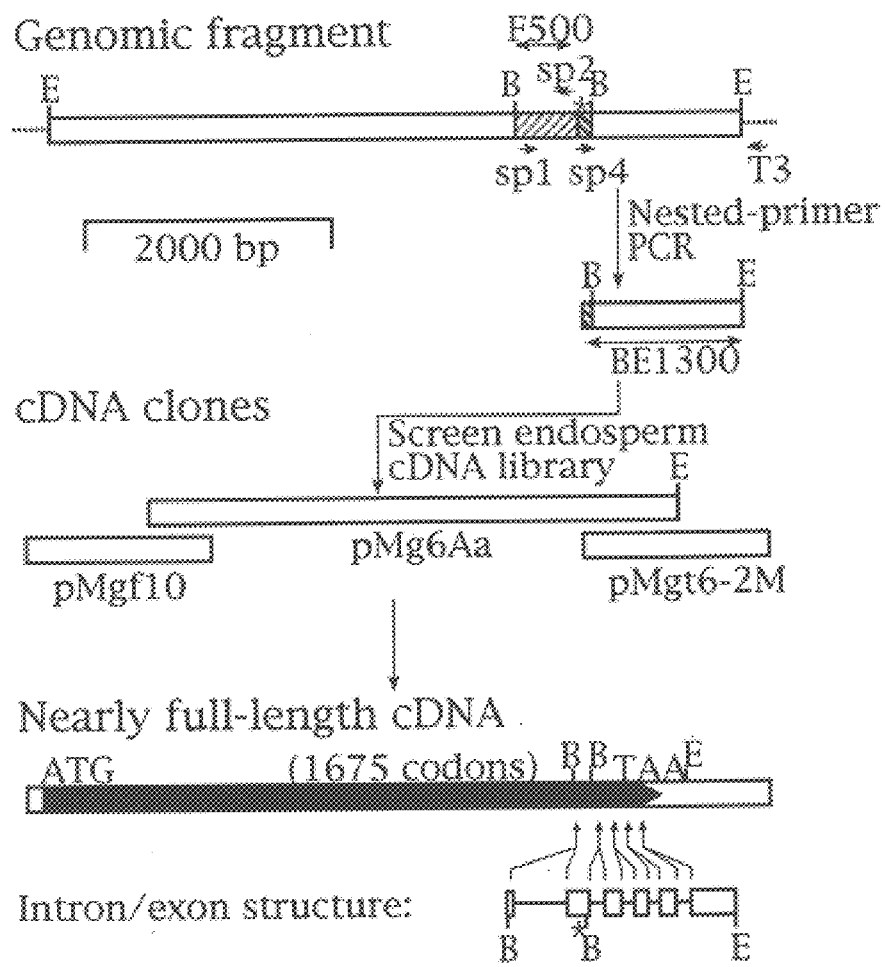
FIG. 3B shows an illustration of the procedure for cloning the near full-length Du1 cDNA. Genomic fragment BE1300 was cloned by nested-primer PCR as detailed below. The wild type counterpart of the original cloned BamHI fragment (indicated by crosshatched boxes) was shown to be part of a 6.0 kb EcoRI fragment in FIG. 3A. A population of EcoRI genomic fragments of about 6.0 kb was ligated to pBluescript SK+ (dashed lines). The ligation mixture was used to amplify a 2.0 kb fragment by primers du1-sp1 and T3. Fragment BE1300 was then amplified from the 2.0 kb fragment by primers du1-sp4 and T3. The position of the Mu1 insertion in du1-R2370::Mu1 is indicated by the asterisk. The positions of PCR primers used for fragment amplification are indicated. Restriction sites are indicated for EcoRI (E) and BamHI (B). The near full-length cDNA diagram represents the continuous sequence from the three overlapping cDNA fragments. The solid arrow indicates the location and 5'-3' direction of the Du1 coding sequence. The partial intron-exon structure was deduced by comparing the available genomic sequence to the cDNA sequence.

Further support for this conclusion is shown in FIG. 3A, which illustrates DNA gel blot analyses of other restriction fragments using fragment F500 as a probe. The size difference of 1.4 kb, indicating a Mu1 insertion, was also observed between the 6.0 kb EcoRI fragment detected both in Du1/du1-Ref plants and du1-2370::Mu1/du1-Ref plants and the 7.4 kb fragment found specifically in the latter. Owing to allelic variation two different XbaI fragments were detected in the Du1/du1-Ref plants of the segregating population. In sibling plants carrying du1-2370::Mu1 the smaller of these two fragments, approximately 3.0 kb in size, invariably was replaced by a fragment 1.4 kb larger. The genomic DNAs used in these two analyses were derived from eight dull kernels and eight normal kernels. In all instances the difference of 1.4 kb between the larger fragment detected solely in plants bearing the mutant allele du1-2370::Mu1 and the smaller fragment associated with the wild type allele Du1 is consistent with insertion of this Mu1 element having caused the du1-mutation. These data also revealed larger genomic fragments that encompass the cloned 2.0 kb BamHI fragment, and thus facilitated isolation of cDNA clones corresponding to the Du1 mRNA.

EXAMPLE 7
Du1 Codes for a Transcript of at Least 6.027 bp

To obtain additional coding sequence for the purpose of screening an endosperm cDNA library, a longer genomic fragment overlapping the cloned 2.0 kb BamHI fragment was isolated from wild type genomic DNA. As described above, a 6.0 kb EcoRI fragment from wild type genomic DNA contains sequences flanking the Mu1 element in the original cloned fragment (FIG. 3A). A 1.3 kb portion of this EcoRI fragment, termed BE1300, was cloned by one-sided, nested-primer PCR amplification. FIG. 3B illustrates that fragment BE1300 extends from within the shorter Mu1-flanking region of the original cloned 2.0 kb BamHI fragment to one of the termini of the 6.0 kb EcoRI fragment. The nucleotide sequence of fragment BE1300 confirmed its overlap with the 2.0 kb BamHI fragment. Fragment BE1300 was then used as a probe to screen a maize endosperm λgt11 cDNA library.

A near full-length cDNA sequence of 6,027 bp was obtained from three overlapping cDNA clones (FIG. 3B). These clones were isolated from three consecutive rounds of screening of approximately $3 \times 10^6$ total pfu of phage. Plasmid pMg6Aa contains a 4.3 kb cDNA insert internal to the near full-length cDNA (nt 1002 to nt 5367), and the cDNA inserts in plasmids pMgf10 (nt 1 to nt 1657) and pMgt6-2M (nt 4433 to nt 6027) overlap and extend the cDNA sequence in this central cDNA fragment at the 5' and 3' ends, respectively (FIG. 3B). The continuous sequence of these three cDNA fragments revealed an ATG-initiated coding sequence of 1674 codons (FIG. 3B). Multiple stop codons in all three reading frames at the 5' end of the cDNA insert of pMgf10 indicate that the coding sequence begins within this fragment. The size of a DNA fragment amplified from endosperm total RNA by 3' RACE indicated that the 3' end of the cloned cDNA is very close to the polyadenylation site(s) of the corresponding transcript. The cloned cDNA, therefore, is nearly-full length and contains the entire coding sequence. This conclusion was supported further by detection of a 6 kb transcript in non-mutant endosperm RNA using the cDNA insert of pMg6Aa as a probe.

EXAMPLE 8
Verification of the Cloned cDNA as a Product of the du1-Locus

Figure 4:
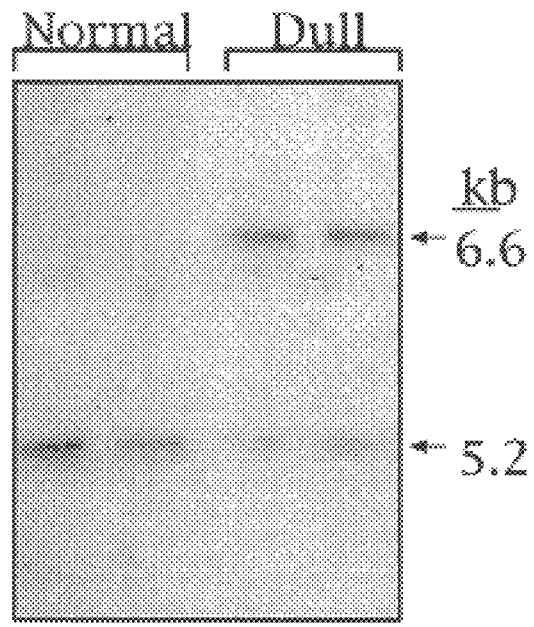
FIG. 4 shows the physical alteration of the cloned locus in plants bearing du1-R2649. Sa1I-digested genomic DNA of seedlings grown from du1-R2649/du1-Ref mutant and sibling Du1/du1-Ref non-mutant kernels was blotted and probed with the cDNA insert from pMgf10.

Physical characterization of another independently isolated du1 allele, du1-R4059, indicated that the cloned cDNA is coded for by the du1 locus, rather than by a different gene closely linked to du1. Genomic restriction fragments from sibling du1-R4059/du1-Ref and Du1/du1-Ref plants (FIG. 1A) were analyzed by DNA gel blot analysis using the cDNA insert of plasmid pMgf10 as the probe. As illustrated in FIG. 4, a 6.6 kb SalI fragment was detected invariably in all plants bearing du1-R4059, in addition to the 5.2 kb fragment that also was the only signal obtained from the Du1/du1-Ref plants. The size shift of 1.4 kb in the SalI fragment associated with du1-R4059 is likely to have resulted from insertion of a Mu1 element. This alteration is distinct from the one associated with du1-R2370::Mu1, because the probe that detects that polymorphism does not identify any abnormal fragment in du1-R4059 mutants (data not shown). The fact that two independent genomic rearrangements in the same gene coincide with appearance of the dull phenotype most likely is explained by Mu1 insertions being the causative agents of the du1- mutations. Accordingly, the cloned cDNA most likely is coded for by Du1. The structure of du1-R2370::Mu1 is consistent with this conclusion. FIG. 3B shows the intron/exon structure deduced by comparing the sequences of the cloned cDNA and genomic fragments. The Mu1 insertion in the cloned 2.0 kb BamHI fragment is within an exon, and thus is expected to disrupt the integrity of the transcript corresponding to the cloned cDNA in du1-R2370::Mu1 endosperm.

Figure 5A:
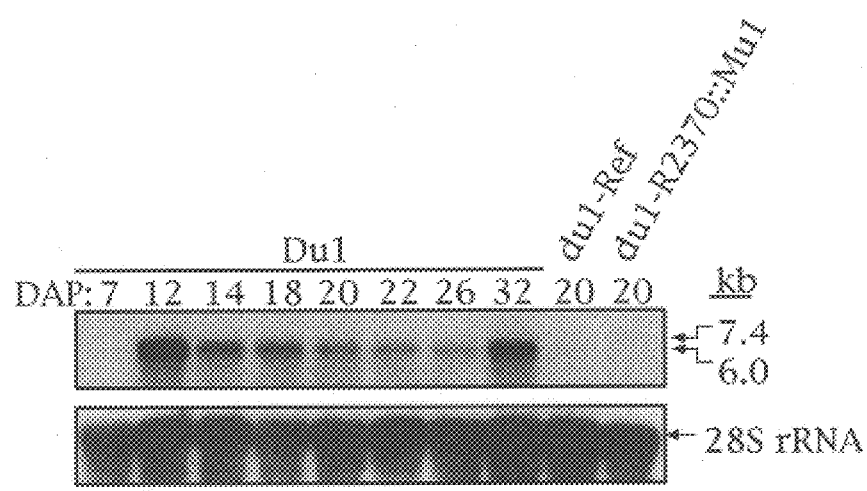
FIG. 5A shows the RNA gel blot analysis of total RNAs from developing endosperm. Total RNAs extracted from endosperm of W64A kernels harvested at various developmental ages, and from du1-Ref and du1-R2370::Mu1 mutant kernels havested at 20 DAP, were fractionated on a formaldehyde-agarose gel, blotted, and probed by the cDNA insert in pMg6Aa. Minor loading differences were calibrated by hybridization of the 26S rRNA on the same blot, stripped of the cDNA probe, to a tomato rRNA cDNA probe. Transcript size was estimated using a RNA size standard (GibcoBRL).
Figure 5B:
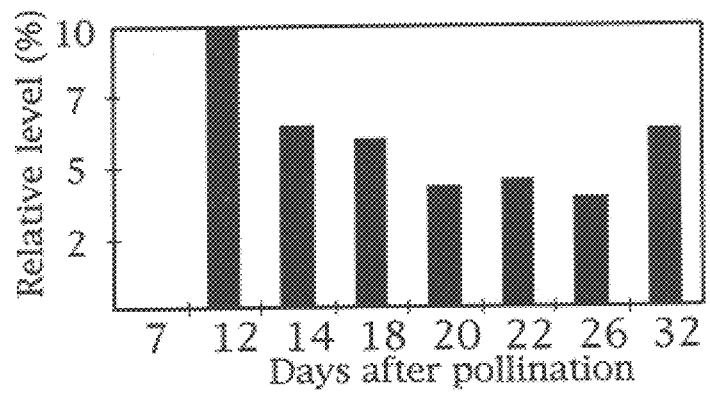
FIG. 5B shows the relative steady state level of the Du1 transcript in developing endosperm. Radioactivity of transcripts hybridized to the Du1 cDNA probe was analyzed using a Phosphorimager, quantified using the program ImageQuant, and expressed as the percentage of the maximal signal strength on the same blot (Relative Level) after calibration of minor loading difference. The data represent the average of three repeats of the analysis with standard error less than 10%.
Figure 5C:
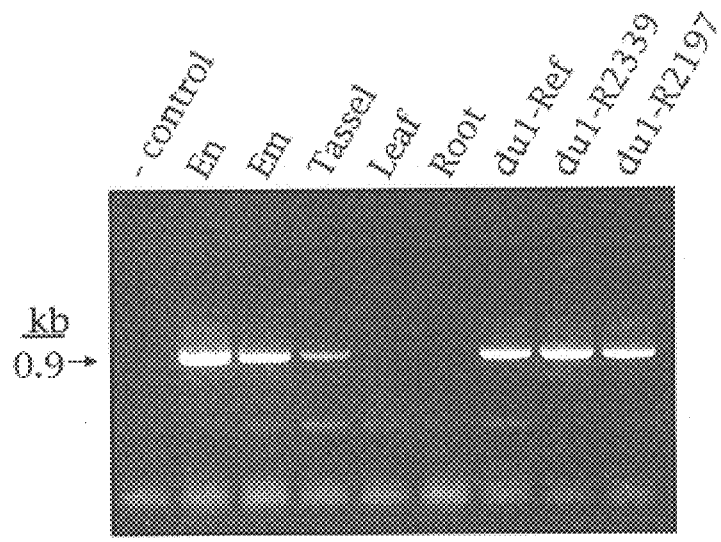
FIG. 5C shows the RT-PCR analysis. DNA fragments amplified from total RNAs by RT-PCR using primers du1-F3 and du1-R1 were separated in an agarose gel and visualized by ethidium bromide staining. Endosperm (En) and embryo (Em) RNAs were from tissue collected 22 DAP. The lane designated "-control" is from the same sample as the En lane, except that the RNA was pretreated with RNAase A prior to amplification. RNAs from the indicated du1- mutants were obtained from endosperm collected 22 DAP.

As predicted, the steady state levels of transcripts hybridizing to the cloned cDNA in du1-R2370::Mu1 and other du1-mutant endosperms were drastically reduced in comparison to non-mutant endosperm of the same developmental age. FIG. 5A shows these results for du1-R2370::Mu1 and du1-Ref endosperm as determined by RNA gel blot analyses using a portion of the cloned cDNA as a probe, and similar data were obtained for du1-R2339 and du1-R2197 endosperms. The residual transcripts in endosperm of du1--R2339 or du1-2370::Mu1 mutants were approximately 1.4 kb larger than normal (FIG. 5A) possibly resulting from transcriptional read-through of the inserted Mu1 element. The residual transcripts hybridizing to the cloned cDNA were of normal size in du1-Ref and du1-R2197 mutant endosperms (FIG. 5A and data not shown). In summary, four independently isolated du1-mutant alleles including du1-Ref are associated with disruption of the transcript detected by the cDNA probe, providing definitive confirmation that Du1 codes for the cloned cDNA. Du1 transcripts were not completely eliminated in endosperm of any of the du1-mutants examined, typical of many maize mutations affecting endosperm starch biosynthesis (Giroux et al., 1994; James et al., 1995; Fisher et al., 1996); FIG. 5C shows that residual Du1 transcripts, although possibly non-functional, were clearly detectable in endosperm of three independent du1- mutants by the more sensitive RT-PCR method, confirming the RNA gel blot results.

EXAMPLE 9
Du1 has a Unique Spatial and Temporal Expression Pattern

Gel blot analysis of total RNA from endosperm of inbred W64A collected at various days after pollination (DAP) revealed a unique temporal expression pattern of a 6.0 kb transcript hybridizing to the Du1 cDNA (FIG. 5A). Du1 transcripts were not detected in endosperm collected at 7 DAP. The transcript level was maximal in endosperm at the early developmental age of around 12 DAP, at which time other starch synthetic genes such as Sbe1, Sbe2b, Bt2, Sh2 and Wx in the same W64A inbred have little or no expression (Gao et al., 1996). The steady state level of the Du1 transcripts declined gradually over time, in contrast to other starch synthetic genes that increase expression as the endosperm develops (Gao et al., 1996). The lowest Du1 transcript level, only about 40% of maximum, was found in endosperm of 22–26 DAP, which has the highest rate of starch synthesis (Jones et al., 1996). The Du1 transcript level rebounded to about 62% of maximum in more mature endosperm of 32 DAP kernels.

Du1 transcript also was detected in other reproductive tissues, specifically embryo and tassel (most likely in pollen). Very low levels of the mRNA were barely detectable by gel blot analysis of total RNAs from these tissues. The presence of Du1 transcripts was demonstrated clearly, however, by the more sensitive RT-PCR analysis (FIG. 5C). The expected 940 bp cDNA fragment was amplified from total RNA extracted from embryo or tassel; this fragment was not amplified from RNase-digested total RNA from 22 DAP endosperm (FIG. 5C), indicating that it was amplified from mRNA rather than from residual contaminating genomic DNA. DNA gel blot analysis using a Du1 cDNA probe confirmed that the 940 bp fragment is amplified from the Du1 mRNA. The additional fragment of approximately 500 bp did not hybridize to the Du1 cDNA probe, and thus is a non-specific amplification product. Du1 transcripts were not detectable by the RT-PCR analysis in total RNAs from leaves and roots (FIG. 5C). These data suggest that the enzyme coded for by Du1 is specialized for the synthesis of storage starch in reproductive organs, but not involved in production of transient starch in leaves.

EXAMPLE 10
Du1 Codes for a Putative Starch Synthase with Conserved Features

The amino acid sequence deduced from the cloned cDNA indicates that Du1 codes for a starch synthase. The longest open reading frame of the continuous Du1 cDNA sequence codes for a polypeptide, termed DU1, of 188 kD including a potential amyloplast transit peptide. Sequence similarity searches found that the deduced amino acid sequence of DU1 is most similar to that of the potato starch synthase SSIII (Abel et al., 1996; Marshall et al., 1996) among all proteins in the public databases.

Figure 6B:
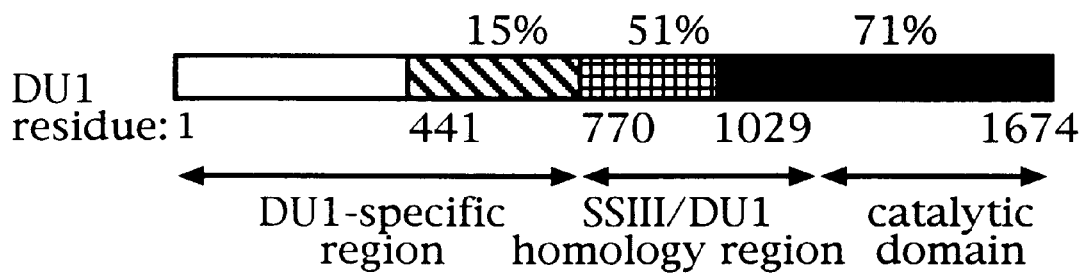
FIG. 6B shows the domains of DU1. Similarity scores between each segment of DU1 and SSIII are shown under each region. "Catalytic domain" indicates the region of DU1 similar in amino acid sequence to $\alpha$-(1→4)-glycosyltransferases in general. "SSIII/DU1 homology domain" indicates the region shared specifically by Du1 and SSIII among known proteins. "Du1-specific region" indicates the portion of DU1 that is unique in amino acid sequence among know proteins.

FIG. 6 shows the alignment of the DU1 and SSIII deduced amino acid sequences, and indicates three discrete regions with varying degrees of similarity between the two proteins. The C-terminal regions, over a span of 645 amino acids (DU1 residues 1029 to 1674), share the highest degree of similarity in the alignment; 73% of the aligned residues are identical in these sequences with only a single gap of one amino acid. In the central regions of DU1 and SSIII, corresponding to DU1 residues 770–1028, 51% of the 259 aligned residues are identical with no gaps in the alignment. This central region was defined by a sharp decrease in the degree of similarity between short stretches of DU1 and SSIII amino acid sequence as the alignment is examined along the lengths of the two proteins. The remaining N-terminal region of DU1 (residues 1 to 769) does not have any significant similarity to that of the potato SSIII, nor to any polypeptide sequence available in the databases. A 440-residue extension relative to SSIII is present in the DU1 N-terminus.

Further comparison of the deduced amino acid sequence of DU1 to cloned starch synthases and glycogen synthases from various species indicates that part of the C-terminal region is likely to provide α-1,4-glycosyltransferase catalytic activity. A stretch of 450 amino acid residues close to the DU1 C-terminus is substantially similar to the corresponding amino acid sequence near the C-termini of many distinct types of α-1,4-glycosyltransferase, including glycogen synthases from E. coli (Genbank accession no. P08323), yeast (Genbank accession nos. M60919 and M65206), and human liver (Genbank accession no. S70004), pea granule-bound starch synthases GBSSI and GBSSII (Genbank accession nos. X88789 and X88790), and maize GBSSI (Genbank accession no. X03935). The degree of sequence conservation in these alignments increases towards the C-termini. As an example, 28% of 438 aligned C-terminal residues are the same in both DU1 and E. coli glycogen synthase, and 67% of the 48 aligned residues of DU1 from position 1550 to 1597 are identical in the corresponding region of the E. coli enzyme with no gaps in the alignment (data not shown). Three sequence blocks are located within this region of DU1 that are highly similar to the conserved regions identified by comparison of E. coli glycogen synthase to GBSSI from a wide variety of plant species (FIG. 6A) (Preiss and Sivak, 1996).

Substantial amino acid sequence conservation at the C-termini of such a phylogenetically divergent group of α-1,4-glycosyltransferases suggests this region of DU1 is highly likely to constitute the complete catalytic domain for such an enzymatic activity. This speculation is further supported by the observation that the central regions of DU1 and SSIII, in which 51% of the amino acids are the same, have no significant similarity to any of the other cloned glycogen synthases or starch synthases. This exclusive sequence conservation, therefore, is expected to define functions belonging solely to a subgroup of plant starch synthases represented by SSIII and DU1. The unique 769 residue sequence at the N-terminus of DU1 is expected to contain an amyloplast targeting peptide and to define functions unique to this enzyme.

EXAMPLE 11
Two Groups of Repeats in the Unique N-terminal Region of DU1

Figure 7A:
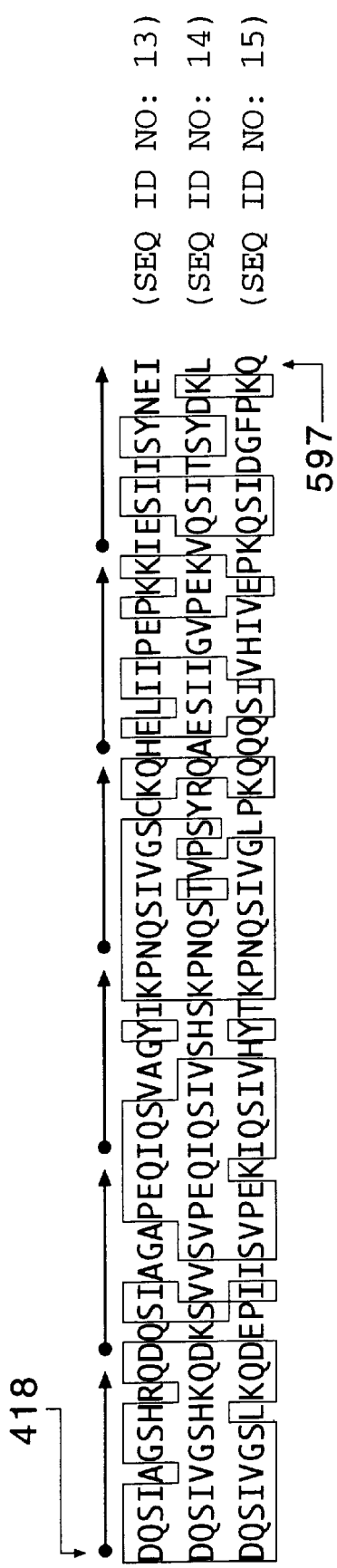
FIG. 7A shows the alignment of the SBE-superrepeats. Numbers refer to positions of residues within the DU1 coding sequence. Each 60 residue SBE-superrepeats comprises six copies of the 10 amino acid SBE-repeat unit (indicated by arrows). The degree of sequence conservation between each SBE-repeat descends toward the C-terminus of each SBE-superrepeat.

FIGS. 6A and 7 show two distinct groups of repeats comprising a total of 180 and 85 amino acids, respectively, that were identified in the unique N-terminal region of DU1 by intra-sequence dot-plot analysis. The larger group of 180 residues (positions 418–597) is a hierarchical repeat. This sequence contains three tandem repeats of 60 residues designated the "SBE-superrepeat", each of which in turn is composed of six tandem repeats of 10 residues designated the "SBE-repeat" (FIG. 7A); these names reflect the fact that the repeating unit is similar to a sequence found in all SBEs. This two-level repeating structure was deduced from the pattern of sequence conservation among the 18 SBE-repeats, i.e., each individual SBE-repeat is most similar to the two repeats positioned either 60 or 120 residues distant (FIG. 7A). Moreover, within single SBE-superrepeats, each individual SBE-repeat is always more similar to the repeat that precedes it in the N-terminal direction than to the one that follows it. These patterns of sequence similarity strongly indicate a hierarchical repeating process involving duplication of the SBE-superrepeat as a unit, rather than 18 individual repeating events. Each SBE-repeat consists of two "half-repeats", of six and four residues, respectively, as deduced from 1) the different degrees of sequence conservation exhibited by the first and second half-repeats among all SBE repeats, and 2) the presence of 4 residues between two complete SBE repeats (FIG. 6A; residues 414–417) probably resulting from an unequal crossover mechanism (Smith, 1976; Lewin, 1997).

The nature of the 180 residue repeat suggests it is involved in a specific function of DU1. The SBE-repeats that begin each SBE-superrepeat are more similar to each other than to the SBE-repeats at any of the other five positions in the superrepeat (FIG. 7A). This suggests that these three SBE-repeats were subjected to the highest selection pressure and thus may represent a functional domain. In contrast, if the first SBE-repeats were not important for function, then mutations should accumulate in those sequences at the same rate that they have appeared in other portions of the SBE-superrepeat, which is not the case. The consensus sequence among these three conserved SBE-repeats is DQSIVG (SEQ ID No. 9) in the first half-repeat, designates as the "M-box", and SHKQ (SEQ ID No. 10) in the second half-repeat. When the M-box sequence was searched for in known polypeptides only a single type of enzyme was found to contain an exact match, namely SBEI family members.

As illustrated in FIG. 7B, the M-box sequence is invariant in maize SBEI, pea SBEII, wheat SBEI, rice RBEI, and potato SBEI. The M-box is well conserved, with substitutions of two residues of similar properties yielding the sequence DQALVG (SEQ ID No. 11), in the corresponding region of SBEII family members including maize SBEIIa and SBEIIb, pea SBEI, rice RBEIII, wheat SBEII, and Arabidopsis SBE2.1 and SBE2.2 (FIG. 7B). The DQALVG sequence also is present in glycogen branching enzymes from yeast and humans (FIG. 7B).

The smaller group of repeats of 85 residues in the N-terminus of DU1 (amino acid 150–233) is composed of three tandem repeats of 28 residues (FIG. 6A and 7C). The basic repeating unit also consists of two halves, 12 and 16 resdiues each, which again are likely to have evolved via imperfect tandem duplications through the unequal crossover mechanism. This conclusion was supported by the distinct degree of sequence conservation of the two half-repeats among the three tandem repeats. The first half-repeat is highly conserved in the first and the third copies of the 28 residue repeat, whereas the second half is more conserved in the first and third copies of the repeats (FIG. 7C).

EXAMPLE 12

Summary

The following four lines of evidence support the conclusion that the genomic locus cloned is a portion of the du1 gene. First, the cloned genomic interval is either within or tightly linked to the du1 locus, because it co-segregated with the dull phenotype in 70 progeny plants. Second, two independent mutations of du1 arose coincidentally with 1.4 kb insertions at distinct positions in the cloned transcription unit, one of which is known to be a Mu1 element located within an exon. Third, transcript hybridizing to the cloned cDNA is reduced drastically to the same extent in endosperm of du1-Ref and three independently isolated du1- mutants. In two of these mutants associated with Mu insertions in du1, the residual transcript is 1.4 kb larger than the wild type mRNA, consistent with insertion of a Mu1 element in an exon. Fourth, the cloned gene codes for a putative starch synthase, consistent with the fact that du1-mutants are greatly reduced in the activity of the soluble starch synthase SSII.

Assuming that the Du1 transcript level reflects enzyme activity, these observations suggest Du1 is involved in starch biosynthesis at a chronologically very early step, possibly closely associated with the initiation event. Conservation of the M-box sequence, the presumed first half-repeat within the amplified SBE-repeat, specifically in starch- and glycogen branching enzymes from phylogentically very divergent species is particularly striking considering that SBEs and SSII act in a concerted biosynthetic pathway. The M-box sequence, therefore, may be a basic structural motif for a particular function shared by all these enzymes, possibly including glucan binding, protein-protein interaction, or serving as regulatory sites. In addition, many consensus sites for N-glycosylation and phosphorylation were found within these repeats, suggesting that they may serve as regulatory sites. The whole group of repeats may form a helix-turn-helix structure, reminiscent of the DNA-binding helix-turn-helix motifs in many transcription factors (Mitchell and Tjian, 1989). Considering the helical architecture of both DNA and $\alpha$-(1→4)-linked glucan polymers, the 85 residue repeat may mediate binding of SSII and associated proteins to growing glucan chains.

Thus, the present invention is directed to an isolated cDNA having the sequence shown in SEQ ID No. 1 encoding a starch synthase II enzyme from maize. Typically, a person with ordinary skill in this art could contruct an expression vector comprising this cDNA, or functional fragments thereof, operably linked to elements that allow expression of the cDNA. Further, one could transfect a host cell with this vector.

The present invention is also directed to a starch synthase II enzyme from maize encoded by this cDNA. The present invention is also directed to a polypeptide encoding a starch synthase II protein, wherein said protein has a molecular weight of approximately 180 kDA, maximal transcript level in endosperm at 12 days after pollination, a C-terminal region possessing $\alpha$-1,4-glycosyltransferase catalytic activity, and an N-terminal region that contains the amyloplast targeting peptide and repeat motifs comprising, but not limited to, the M-box (SEQ ID No. 9). In one embodiment, the protein has the amino acid sequence shown in SEQ ID No. 12.

The present invention is also directed to an antibody directed towards the polypeptide described herein, or functional fragments thereof.

In a separate embodiment, a person having ordinary skill in this art could manipulate a plant to create a transgenic plant, having as the transgene is the vector described above. Using this technology, one could produce starch, comprising the steps of: transforming a cell with the vector of claim 2; and extracting and purifying said starch. Preferably, the cells carry a mutation. Representative examples of useful mutations include a gene encoding an enzyme involved in starch synthesis, starch metabolism, glucose synthesis, glucose metabolism, glycogen synthesis, glycogen metabolism, carbohydrate synthesis and carbohydrate metabolism.

Manipulation of the enzymatic machinery of starch production in higher plants can be used to create starch forms that have specific branching patterns and specific chain lengths. Properties of chain length and/or degree of branching confer specific characteristics on starch such as swelling, polarity, water retention, clarity, ability to disperse pigments, and freeze-thaw properties. The production of tailored starches with defined and predictable properties is expected to be useful for a variety of specific food and industrial applications. Altering the activity of the DU1 starch synthase through the transgenic approaches listed below can be used to create novel starch forms with chain lengths and/or branching patterns that differ from those in traditional starches. For example, one can modify starch in transgenic plants by the over-expression of DU1 starch synthase. Secondly, one could modify starch in transgenic plants by reducing or eliminating the expression of DU1 starch synthase, either by 1) introduction of DU1 in the antisense orientation, or by 2) cosuppression of DU1 resulting from over-expression of the DU1 transgene the over-expression of Du1 starch synthase. Thirdly, one could modify starch in transgenic plants by the introduction of an altered Du1 sequence, thereby producing an altered DU1 protein. Fourthly, one could modify starch in transgenic plants by the introduction of a polypeptide fragment of the DU1 protein, or by introduction of a polypeptide fragment of the DU1 protein in the antisense orientation, or by introduction of an altered polypeptide fragment of the DU1 protein. Additionally, one could modify glycogen production in transformed bacterial and/or yeast cells by the expression of DU1 starch synthase. DU1 expression may be placed under the control of constitutive or inducible promoters. One could propagate the transgenic plants to produce a described starch form with specific characteristics, or cross the transgenic plants with plants in distinct genetic backgrounds or which have distinct genetic traits to produce additional altered starch forms. These starches could be marketed for their unique features to various industries; for example, as food or beverage additives, or as processing agents in the manufacturing of paper or textiles. Also, a licensee could grow recombinant yeast or bacteria engineered to express DU1 starch synthase in large-scale to produce an altered glucan which would have industrial utility.

Also provided by the present invention are polypeptide fragments comprising regions of the DU1 starch synthase recognized by an antibody specific for a DU1 determinant. A polypeptide which comprises a DU1 fusion protein could also be prepared by one having ordinary skill in this art as is an antibody reactive with the DU1 protein or polypeptide fragments.

One having ordinary skill in this art could also prepare a transgenic plant comprising a genome including a foreign DNA sequence encoding the DU1 protein under the control of its own promoter or another promoter; or including a sequence encoding DU1 modified to produce altered DU1 activity.

The following references were cited herein:

Abel, G. J. W. et al. (1996). Plant J. 10, 981–991.
Ausubel, F. M. et al (1989). Current Protocols in Molecular Biology. (NY: John Wiley and Sons).
Bae, J. M. et al. (1990) Maydica 35, 317–322.
Ball, S. et al. (1996). Cell 86, 349–352.
Barker, R. F. et al. (1984). Nucl. Acids Res. 12, 5955–5967.
Beavis, W. et al. (1995). Maize Genet. Coop. Newsl. 69, 182–184.
Bhave, M. R. et al. (1990). Plant Cell 2, 581–588.
Boyer, C. D. et al. (1977). Amer. J. Bot. 64, 50–56.
Boyer, C. D., and Preiss, J. (1978a). Carbohydr. Res. 61, 321–334.
Boyer, C. D., and Preiss, J. (1978b). Biochem. Biophys. Res. Commun. 80, 169–175.
Boyer, C. D., and Preiss, J. (1981). Plant Physiol. 67, 1141–1145.
Boyer, C. D. et al. (1976). Cereal Chem. 53, 327–337.
Cameron, J. W. (1947). Genetics 32, 459–485.
Chou, P. Y., and Fasman, G. D. (1978). In Advances in Enzymology, A. Meister, ed (NY: John Wiley and Sons), pp. 45–148.
Church, G. M., and Gilbert, W. (1984). Proc. Natl. Acad. Sci. USA 81, 1991–1995.
Creech, R. G. (1965). Genetics 52, 1175–1186.
Creech, R. G., and McArdle, F. J. (1966). Crop Sci. 6, 192–194.
Dang, P. L., and Boyer, C. D. (1988). Phytochemistry 27, 1255–1259.
Davis, J. H. et al. (1955). Argon. J. 232–235.
Dvonch, W. et al. (1951). Cereal Chem. 28, 270–280.
Fisher, D. K. et al. (1993). Plant. Phsiol. 102, 1045–1046.
Fisher, D. K. et al. (1996). Plant Physiol. 110, 611–619.
Fisher, D. K. et al. (1995). Plant Physiol. 108, 1314–1314.
Fontaine, T. et al. (1993). J. Biol. Chem. 268, 16223–16230.
French, D. (1984). In Starch: Chemistry and technology, R. L. Whitaker, ed (Orlando: Academic Press), pp. 183–248.
Gao, M. et al. (1996). Plant Mol. Biol. 30, 1223–1232.
Gao, M. et al. (1997). Plant. Physiol. 114, 69–78.
Garnier, J. R. et al. (1978). J. Mol. Biol. 120, 97–120.
Giroux, M. J. et al. (1994). Plant Physiol. 106, 713–722.
Hannah, L. C. et al. (1993). Sci. Hortic. 55, 177–197.
Inouchi, N. et al. (1987). Starch/Staerke 39, 259.
James, M. G. et al. (1995). Plant Cell 7, 417–429.
Jespersen, H. M. (1993). J. Prot. Chem. 12, 791–805.
Jones, R. J. et al. (1996). Crop Sci. 36, 301–306.
Klösgen, R. B. et al. (1986). Mol. Gen. Genet. 203, 237–244.
Konat, G. W. et al. (1994). In PCR Technology, Current Innovations, H. G. G. Griffin and M. Annette, eds (Boca Raton, Fla.: CRC Press), pp. 37–42.
Kuriki, T. et al. (1996). J. Prot. Chem. 15, 305–313.
Lewin, B. (1997). Genes VI. (Oxford: Oxford University Press).
Mangelsdorf, P. C. (1947). Genetics 32, 448–458.
Manners, D. J. (1989). Carbohydrate Polymers 11, 87–112.
Marshall, J. et al. (1996). Plant Cell 8, 1121–1135.
Martin, C., and Smith, A. M. (1995). Plant Cell 7, 971–985.
Mitchell, J. P., and Tjian, R. (1989). Science 245, 371–378.
Mu, C. et al. (1994). Plant J. 6, 151–159.
Nelson, O. E., and Pan, D. (1995). Annu. Rev. Plant. Physiol. Plant Mol. Biol. 46, 475–496.
Ozbun, J. L. et al. (1971). Plant Physiol. 78, 765–769.
Preiss, J. (1991). Oxford surveys of plant molecular and cell biology 7, 59–114.
Preiss, J., and Sivak, M. (1996). In Photoassimilate Distribution in Plants and Crops, E. Zamski and A. A. Schaffer, eds (New York: Marcell Dekker, Inc.), pp. 63–96.
Robertson, D. S. (1978). Mutat.Res. 51, 21–28.
Sambrook, J. et al. (1989). Molecular Cloning. A Laboratory Manual. (Plainview, N.Y.: Cold Spring Harbor Laboratory Press).
Shannon, J. C., and Garwood, D. L. (1984). In Starch. Chemistry and Technology, R. L. Whistler, J. N.

BeMiller and E. F. Paschall, eds (San Diego: Academic Press, Inc.), pp. 25–86.

Shure, M. et al. (1983). Cell 35, 225–233.

Smith, A. et al. (1996). Annu. Rev. Plant Physiol. Plant Mol. Biol. 48, 67–87.

Smith, G. P. (1976). Science 191, 525–535.

Stinard, P. S. et al. (1993). Plant Cell 5, 1555–1566.

Takeda, et al. (1993). Carbohydr. Res. 240, 253–363.

Wang, Y. -J. et al. (1993a). Cereal Chem. 70, 521–525.

Wang, Y. -J. et al. (1993b). Cereal Chem 70, 171–179.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. The isolated cDNA of SEQ ID NO: 1 encoding a starch synthase II enzyme from maize.

2. An expression vector comprising the cDNA of claim 1, or functional fragments therefrom, operably linked to elements that allow expression of said cDNA.

3. A host cell transfected with the vector of claim 2.

4. A starch synthase II enzyme from maize encoded by the cDNA of claim 1.

5. A transgenic plant, wherein the transgene is the vector of claim 2.

* * * * *